(12) United States Patent
Schmieding et al.

(10) Patent No.: US 7,507,231 B2
(45) Date of Patent: Mar. 24, 2009

(54) SURGICAL POWER CONSOLE WITH LOCKING SPEED CONTROL

(75) Inventors: Reinhold Schmieding, Naples, FL (US); Randall L. Hacker, Naples, FL (US)

(73) Assignee: Arthrex, Inc., Naples, FL (US)

( * ) Notice: Subject to any disclaimer, the term of this patent is extended or adjusted under 35 U.S.C. 154(b) by 375 days.

(21) Appl. No.: 11/019,200

(22) Filed: Dec. 23, 2004

(65) Prior Publication Data
US 2005/0149004 A1 Jul. 7, 2005

Related U.S. Application Data

(60) Provisional application No. 60/531,626, filed on Dec. 23, 2003.

(51) Int. Cl.
*A61B 17/00* (2006.01)
(52) U.S. Cl. .............................. 606/1; 606/79; 606/80; 606/82; 606/84
(58) Field of Classification Search ...................... 606/1
See application file for complete search history.

(56) References Cited

U.S. PATENT DOCUMENTS 6,017,354 A 1/2000 Culp et al.
6,447,503 B1* 9/2002 Wynne et al. .................. 606/9

* cited by examiner

*Primary Examiner*—Lee S Cohen
(74) *Attorney, Agent, or Firm*—Dickstein Shapiro LLP

(57) ABSTRACT

A powered surgical system includes a power console with locking speed control capabilities. The surgical power console delivers power to two separate surgical instruments, particularly surgical handpieces used in orthopedic procedures. The user/console interface includes footswitches, handpiece mounted switches, and front panel controls. The console provides controls for speed and direction of the handpiece, as well as the ability to switch directions on a variable time basis. Advantageously, the console provides a "cruise control" capability which locks in the speed of a particular handpiece. Once the cruise control option is selected, the surgeon can engage the cruise control function simply by using a "gas pedal" footswitch. Once a desired handpiece speed is established, the surgeon's foot can be removed from the footswitch, allowing the surgeon greater comfort, greater range of motion, and improved access to the operational situs. Disengagement of cruise control is achieved easily by actuating any of the foot control or front panel switches, for example.

2 Claims, 2 Drawing Sheets

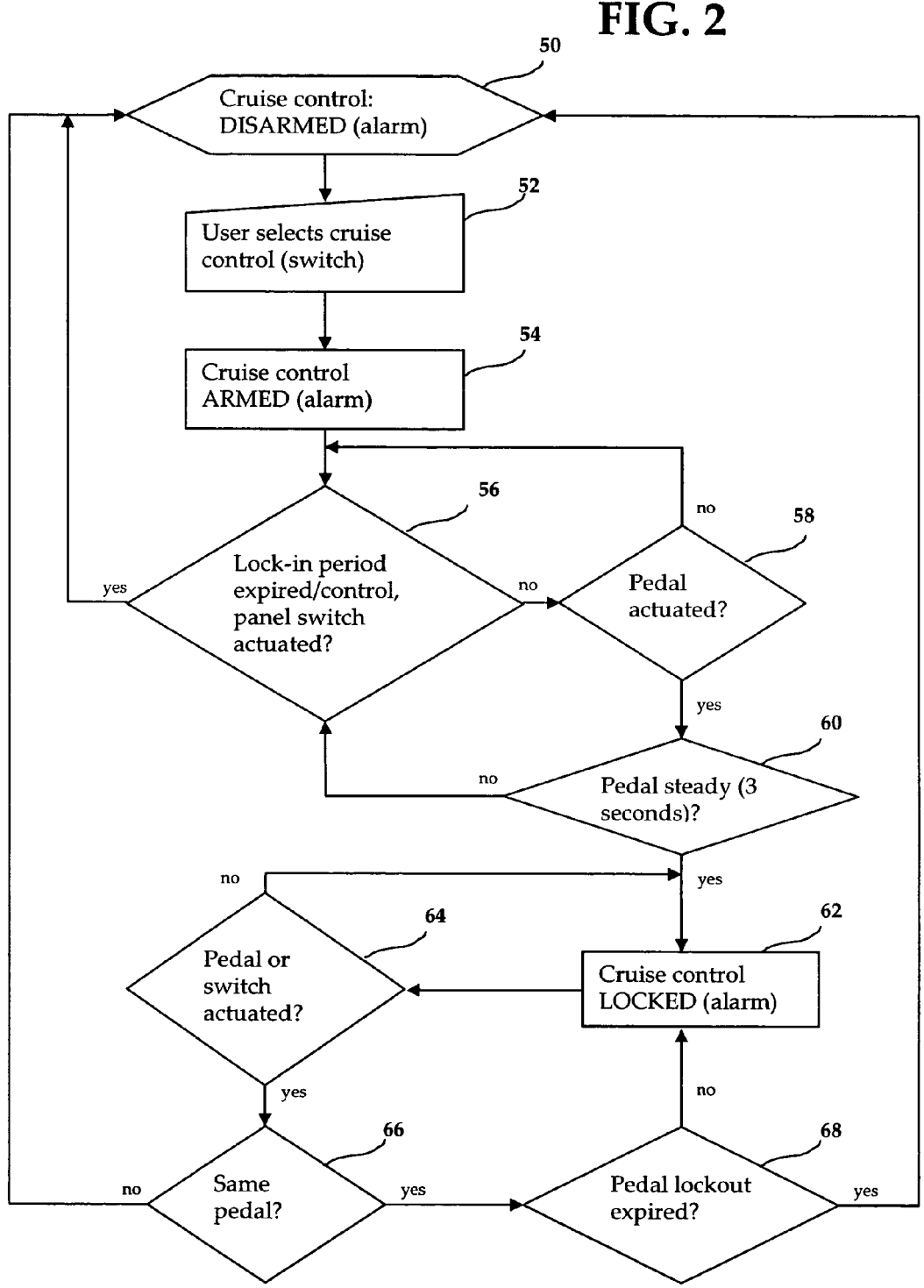

SURGICAL POWER CONSOLE WITH LOCKING SPEED CONTROL

This application claims the benefit of U.S. provisional application No. 60/531,626 filed Dec. 23, 2003 and incorporated herein by reference.

BACKGROUND OF THE INVENTION

The present invention relates to surgical power consoles, and, more specifically, to surgical power consoles with locking speed control capabilities.

BRIEF SUMMARY OF THE INVENTION

The present invention provides a surgical power console with locking speed control capabilities. The surgical power console delivers power under individual control to two separate surgical instruments, particularly surgical handpieces used in orthopedic procedures. The control console delivers appropriate power to the handpieces, and provides protection schemes to prevent handpiece overheating, for example. Identification of the type of handpiece by the console provides appropriate user selectable setting controls and displays. The user/console interface includes footswitches, handpiece mounted switches, and front panel controls. The console provides controls for speed and direction of the handpiece, as well as the ability to switch directions on a variable time basis. Advantageously, the console provides the ability to lock in a particular handpiece speed, referred to herein as "cruise control."

BRIEF DESCRIPTION OF THE DRAWINGS

FIG. 2 is a flow chart showing the cruise control operational mode of the surgical power console of FIG. 1.

DETAILED DESCRIPTION OF THE INVENTION

Figure 1:
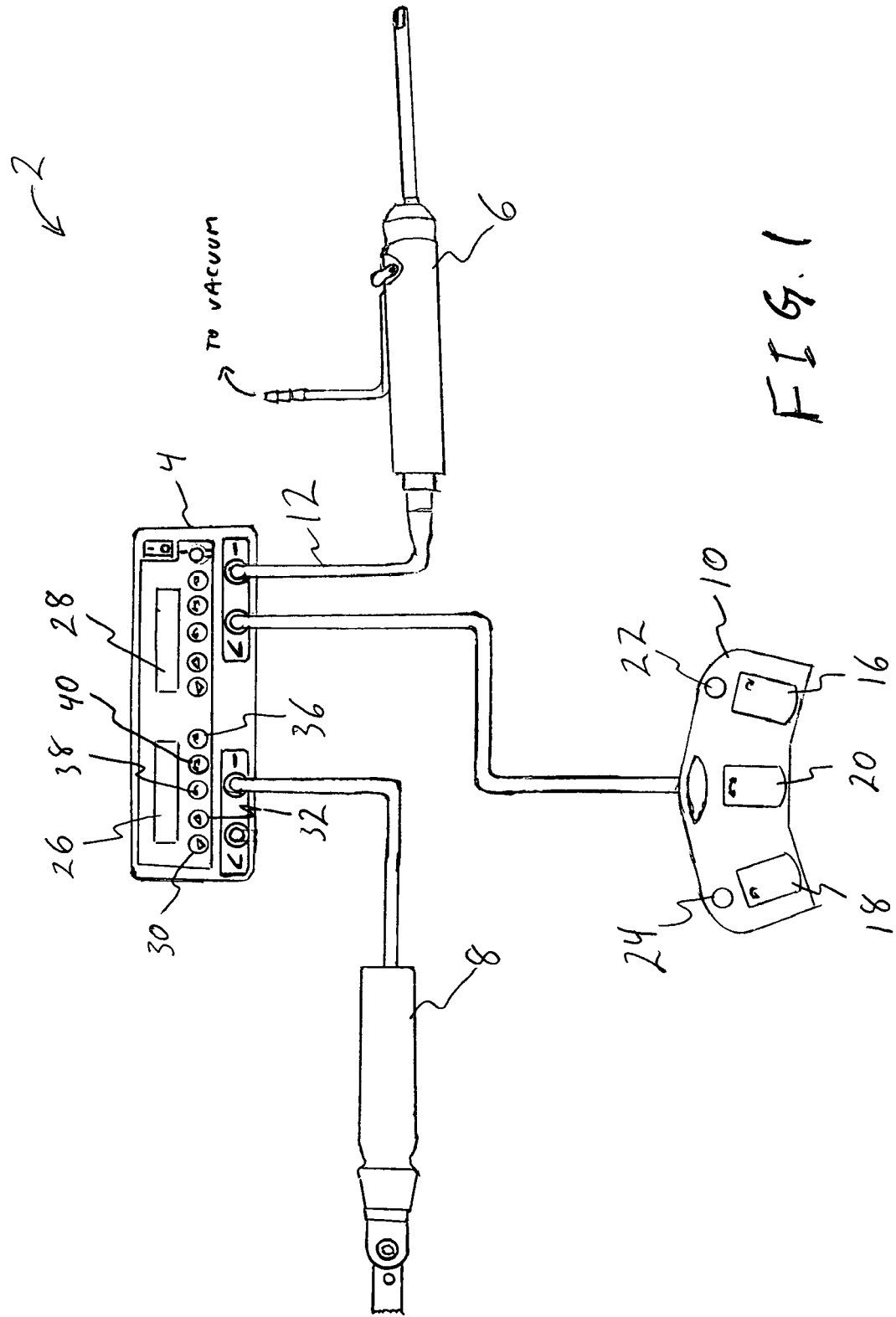
FIG. 1 is a schematic illustration of a surgical power console with attached handpieces and footswitch controls according to an exemplary embodiment of the present invention.

Referring to FIG. 1, a powered surgical system 2 is illustrated. The surgical system 2 is designed to accommodate a variety of handheld powered instruments to assist a surgeon in performing multiple types of orthopedic procedures. An exemplary surgical power console 4 features two fully functional handpiece channels that allow simultaneous handpiece operation under individualized control. Each of the handpieces utilizes a four-pole, three-phase brushless DC motor. Adequate power supply and protection schemes to prevent handpiece overheating are provided.

As illustrated in FIG. 1, a shaver 6 and a sagittal saw 8 are connected to the console 4. Both handpiece channels can be operated with a single footswitch 10. Alternatively, the handpieces can be operated by separate footswitches by way of a second footswitch is connected to the console.

The surgical power console 4 has a maximum speed of 8,000 revolutions per minute, and provides precise shaver burr control for example, during surgical procedures. A universal power supply used in the power console 4 allows AC voltages ranging from about 100 to about 240 VAC, with frequencies in the range of about 47-63 Hz. The supply meets all currently established medical safety requirements. The maximum power output is 8 amps at 48 volts (384 watts) with two handpieces running simultaneously. It is assumed that this is an extreme and short-term condition. The drill is the only attachment that is capable of using 4 amps and only for 30 seconds. The other handpieces require 3 amps maximum and 2 amps average loading. The expected average power requirement is 4 amps at 48 volts (192 watts). 48V power supply accuracy is 2%.

Handpiece selections and speeds are set forth in Table 1, as follows:

TABLE 1

| Handpiece | Speed Range | Accuracy |
|---|---|---|
| Shaver | 300-8000 rpm | 5% or +/− 100 rpm (greater of the two) |
| Shaver 5 | 300-8000 rpm | 5% or +/− 100 rpm (greater of the two) |
| Small Joint Shaver | 300-8000 rpm | 5% or +/− 100 rpm (greater of the two) |
| Drill | 100-1400 rpm | 5% or +/− 20 rpm (greater of the two) |
| Sagittal Saw | 18000 rpm | 6% |

The handpiece 6 has a dedicated cable 12 for maximum durability. A separate autoclavable cable 14 is attached to the saw 8, or an optional drill (not shown), and can be switched easily between the two in the sterile field providing ultimate system flexibility. Advantageously, a surgical assistant can perform preparatory tasks with one handpiece while the surgeon is operating with the other.

The low profile, waterproof footswitch 10 provides precise control of all power functions without causing fatigue in the surgeon/operator. A "gas pedal" footswitch 10 provides the ability to change blade or burr speeds on handpiece 6 simply by changing the amount of pressure applied to the pedals 16, 18, 20. Pedal 16 controls the clockwise rotational speed of a rotatable handpiece, such as shaver 6. Pedal 18 controls the counterclockwise rotational speed of the rotatable handpieces. Pedal 20 controls the speed of handpieces that operate in an oscillatory mode, with directional operation changing repeatedly from clockwise to counterclockwise.

A cruise control switch 22 on the footswitch 10 activates a constant speed function for the selected handpiece, described in more detail below. The cruise control function allows the surgeon to lock the handpiece speed for continuous operation during lengthy procedures without the need to continually depress a pedal using a constant pressure, thereby reducing surgeon fatigue. The cruise control function is engaged by depressing the cruise control switch, and disengaged by pressing any foot pedal. A toggle switch 24 is provided to control each of the channels when two handpieces are connected to the console 4 and are controlled by only one footswitch 10.

Two banks of control switches located on the front panel of power console 4 provide control features corresponding to pedals 16, 18, 20. Thus, speed control switches 30, 32 increase and decrease speed, respectively, for the left channel. Directional control switches 36, 38, 40 allow selection of clockwise, counterclockwise, and oscillatory motion for the left channel. Identical control switches are provided for the right channel.

The gas pedal footswitch 10 will be described in greater detail, as follows: The cruise control switch 22 and the toggle switch 24 on footswitch 10 each are provided as a separate momentary contact switch that is normally open. The switch preferably is actuated by foot-applied pressure to close. Each cruise control switch 22 and toggle switch 24 provides an active low signal. The three speed control pedals 16, 18, 20 give a continuously variable analog voltage output related to position. Voltage output from about 0.0 to 10.0 volts generates minimum to maximum speeds.

Each handpiece has a defined minimum and maximum speed based on the handpiece operating modes and capacities. Software provided within the console microprocessor logic is used to divide the voltage ranges provided into at least 248 levels. The software preferably divides the range into over 1,000 levels, for example, using the processor's 10-bit A/D capacity. The voltage is divided and applied to one of the A/D input port pins on a microprocessor of the power console 4Additionally, the software performs hysteresis on the input, and maintains "soft limits" for pedal-on and full-scale voltages, corresponding to minimum and maximum speeds. These are currently set as shown in Table 2 below:

TABLE 2

| Hysteresis (RPM) | Footswitch "on" voltage | Footswitch "full-scale" voltage |
|---|---|---|
| 30 | 0.5 v | 4.4 v |

The cruise control function will be described in greater detail with reference to FIG. 2. The cruise control function begins in a DISARMED state, as shown at step 50. Cruise control operational mode is initiated by depressing at step 52 the cruise control switch 22 on the gas pedal style footswitch 10. If the cruise switch is actuated on an attachment that does not allow cruise control, and audible error beep occurs (3 fast beeps, 50 ms on/50 ms off), and a momentary message "*CRUISE NOT ALLOWED*" is displayed on a respective one of the front display screens 26, 28 located on the front panel of control console 4, shown in FIG. 1.

Referring again to FIG. 2, the cruise control operation proceeds as follows:

1. Cruise Set—When selected by the cruise control switch 22, the cruise function becomes ARMED (signified by a single audible one second beep), as shown at step 54. Once the cruise function has been ARMED, a LOCK IN period is provided during which the user can actuate one of the console controls, such as one of the three pedals, to engage cruise control. A determination is made at decision step 56 regarding the status of the LOCK IN period. If a pedal, for example, is not actuated within 15.0 seconds, the LOCK IN period expires, and the cruise function becomes DISARMED (signified by a single audible 1 second beep). Once the cruise function has become DISARMED, the cruise control switch requires re-activation in order to re-ARM the cruise function.

2. Cruise Lock—During the LOCK IN period, which lasts for up to 15 seconds, for example, the operator actuates the foot switch (step 58) and adjusts the speed of the selected handpiece. The operator can then hold a selected pedal (16, 18, or 20) steady for 3 seconds (step 60) to engage the LOCKED state (step 62). Once in the LOCKED state, the handpiece will operate at the selected speed without the necessity of the operator holding the pedal or foot switch. Steady is defined as +/−500 RPM for forward/reverse, and +/−400 RPM for oscillation. If the pedal is held steady, the console emits an audible double beep (100 ms on/100 ms off) that indicates the LOCKED state has been entered, and the corresponding display indicates "*LOCK*." If the pedal was not held steady within the 15 second LOCK IN period, the cruise function becomes DISARMED (signified by a single audible 1 second beep).

3. Remove Foot—Once LOCKED cruise control operation has been established, the selected handpiece will run at the selected speed until the cruise control is DISARMED. The cruise control can be DISARMED by actuating any of the foot and panel controls on the console, as shown in step 64, with one important exception: The console logic, controlled by a microprocessor for example, preferably provides a limited pedal lockout period.

The pedal lockout period provides a window of opportunity during which the operator's foot can be removed from the selected pedal, as shown at steps 66 and 68. A three second window, for example, is provided during which movement of the selected pedal used to activate the LOCKED speed control will not DISARM cruise control operation. The pedal lockout period is necessary as the act of removing the foot from the pedal results in pedal movement, which otherwise would register as a signal to shut off the cruise control mode, as noted above and described further below. During the pedal lockout period, only the selected pedal is isolated from movement detection by the console.

Once the selected pedal is fully released or three seconds has elapsed (whichever comes first), the system again responds to operation of the selected pedal, whereby cruise control function can be disarmed by movement of the selected pedal. In the meantime, at any time during or after the 3 second window for selected pedal lockout (i.e., during the cruise control LOCKED state) if any other pedal, foot switch, panel switch, or handpiece switch besides the selected pedal is activated, the cruise control function for that channel will DISARM.

4. Disable Cruise Lock—If any pedal, foot switch or panel switch is activated on the channel while in the LOCKED state, the cruise function becomes DISARMED (with the exception noted in item 3 "Remove Foot").

5. Disable Cruise Set—If the toggle, cruise control, or front panel switches are actuated at any time after the cruise control switch is selected (i.e., in the ARMED or LOCKED condition) then the cruise function becomes DISARMED, as shown at step 56.

The power console and control systems have been described with respect to particular exemplary embodiments of the present invention. The invention is not limited, however, to application in surgical instruments, for example. Power consoles and control systems according to the present invention can be used with handheld instruments in non-surgical settings, such as manufacturing, for example. The power consoles and control systems also can be used with various the types of handpieces, both medical and otherwise, such as hand-held instruments used to apply various types of radiation such as light and heat, including electrosurgical instruments, for example.

The above description and drawings illustrate preferred embodiments which achieve the objects, features, and advantages of the present invention. Although certain advantages and preferred embodiments have been described above, those skilled in the art will recognize that substitutions, additions, deletions, modifications and/or other changes may be made without departing from the spirit or scope of the invention.

What is claimed as new and desired to be protected by Letters Patent of the United States is:

1. A method of controlling a surgical handpiece using a power console operating under processor-based control, the method comprising:

arming a cruise control function of the power console for controlling the surgical handpiece;

providing a lock-in period during which the cruise control function remains armed;

sensing an input from an initial actuator;

determining if the input from the initial actuator remains steady for a period of time; and locking on the cruise control function, for at least a lockout period, based on the determination, wherein during the lockout period the cruise control function cannot be disarmed.

2. A method as in claim 1, further comprising:

sensing for an input from a second actuator with the cruise control function locked;

determining whether the second actuator is the same as the initial actuator, and if so, determining whether the lockout period has expired; and disarming the cruise control function if the lockout period has expired.

\* \* \* \* \*